(12) United States Patent
Shams

(10) Patent No.: US 8,512,299 B2
(45) Date of Patent: Aug. 20, 2013

(54) ATTACHMENT FOR A PARENTERAL DEVICE

(76) Inventor: Iden Shams, London (GB)

( * ) Notice: Subject to any disclaimer, the term of this patent is extended or adjusted under 35 U.S.C. 154(b) by 57 days.

(21) Appl. No.: 12/680,871

(22) PCT Filed: Sep. 11, 2008

(86) PCT No.: PCT/GB2008/050816
§ 371 (c)(1),
(2), (4) Date: Mar. 30, 2010

(87) PCT Pub. No.: WO2009/044182
PCT Pub. Date: Apr. 9, 2009

(65) Prior Publication Data
US 2010/0217207 A1 Aug. 26, 2010

(30) Foreign Application Priority Data
Oct. 4, 2007 (GB) .................................. 0719430.1

(51) Int. Cl.
*A61M 5/31* (2006.01)
(52) U.S. Cl.
USPC .......................................... 604/240; 604/195
(58) Field of Classification Search
USPC ................. 604/240, 181, 187, 192–198, 110, 604/263
See application file for complete search history.

(56) References Cited

U.S. PATENT DOCUMENTS 5,498,245 A * 3/1996 Whisson ....................... 604/198
5,704,921 A 1/1998 Carilli

FOREIGN PATENT DOCUMENTS

| EP | 0479303 | 4/1992 |
|---|---|---|
| EP | 0613382 | 9/1994 |
| EP | 1161962 | 12/2001 |
| WO | WO92/17230 | 10/1992 |
| WO | WO93/09824 | 5/1993 |
| WO | WO96/10433 | 4/1996 |
| WO | WO98/20922 | 5/1998 |
| WO | WO2006/111806 | 10/2006 |
| WO | WO2007/131282 | 11/2007 |

* cited by examiner

Primary Examiner — Bhisma Mehta
Assistant Examiner — Phillip Gray
(74) Attorney, Agent, or Firm — Thorpe North & Western LLP (57) ABSTRACT

An attachment for a parenteral device, the device comprising a body and an outlet for conveying fluid, the attachment comprises a housing (12) adapted for engagement with the body, an elongate hollow needle (30), having an outer end (32) and an inner end (34), with an aperture at both ends, a carrier (40) for carrying the needle, the carrier being movable relative to the housing from a first, position, at which the outer end is received within the housing, to a second position at which the outer end extends from the housing and the carrier being movable from second position to first position, and the housing having a flow path extending, when the carrier is in second position, between the outlet and the carrier, wherein the needle is open at the inner end; whereby when the carrier is positioned in second position the inner end is brought into communication with the flow path.

13 Claims, 10 Drawing Sheets

ATTACHMENT FOR A PARENTERAL DEVICE

FIELD OF THE INVENTION

This invention relates to an attachment for a parenteral device.

REVIEW OF THE ART KNOWN TO THE APPLICANT AND PROBLEMS TO BE SOLVED

Attachments to parenteral devices are known. Of those attachable devices, there is a subclass of retractable needle devices for syringes. The nearest known prior art to the invention contained within this specification is to be found at patent EP 0 613 382. The parenteral device contained within that patent specification has a number of problems. The device is reproduced at FIG. 1 of the diagrams contained within this application.

Figure 1:
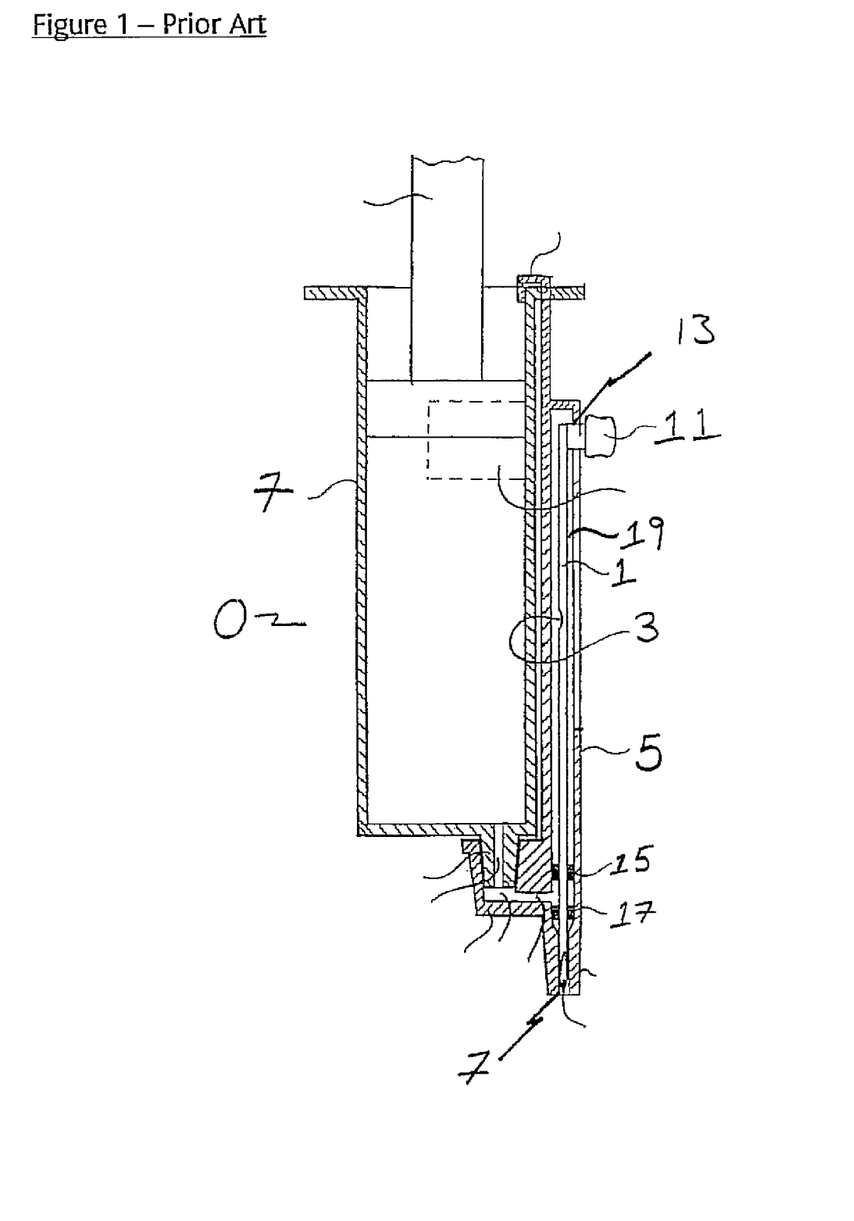
FIG. 1 is a cross-sectional side view of the prior art.

The device, indicated generally at 0, features a needle 1 which is part of a needle body with a second aperture 3 provided at an intermediate position along its length. It is this second aperture 3 which completes the flow path between the parenteral device 7, which in this case is a syringe, and the needle 1 itself. The provision of this second aperture 3 is problematic for a number of reasons. The first is that the making of the needles is costly and difficult, as needles used with syringes are made of high grade steel, are relatively narrow in diameter and, significantly, are circular cylindrical. The confluence of these factors makes it exceedingly difficult for the manufacturer to make perforations in the needles, either by drilling or by other means. Such difficulty leads to a large increase in time and cost of manufacture.

A second problem with the needle body of EP 0 613 382 is that of assembly, both in terms of initial assembly and the subsequent repair and replacement of elements of the parenteral device. At FIG. 1, in order to introduce needle 1 into housing 5, one would have to thread it through narrow aperture 7, then through even narrower sealing means 15 17, making sure that the needle 1 itself does not damage the sealing means 15 17. Then you would have to orientate needle 1 in such a way that aperture 3 would be brought into line with flow path 9 when needle 1 is brought into the extended position, and then attach handle 11 to the end of the needle 1, through handle receiving aperture 13. This is a complex and precise operation and therefore both time consuming and costly. There is a need, therefore, to supply a design for an attachment which the fabricator and the user are able better to assemble and disassemble the device, for manufacturing, repairing and cleaning purposes.

Third, EP 0 613 382 features sealing means 15, 17 which keep the flow path 9 sealed, by blocking the space either side of the needle 1 in the cavity 19 of the housing 5. However, even though sealing means 15, 17 are so fashioned to provide a watertight fit, it is unlikely that the fit is so good that no contaminants would be able to pass beyond the upper part 15 of the sealing means, into the largest part of the cavity 19 of the housing 5. Because the fit is watertight, it is impossible to pass fluid into the largest part of the cavity, and therefore it is very difficult to remove the build-up of contaminants or otherwise clean the device 0. This may be dangerous when the device is to be reused. The user may also be given the incorrect impression that the needle is clean by the fact that it is retracted.

Devices utilising needles featuring such an unusually positioned side aperture must ensure that this very small aperture is positioned so as to form a fluid pathway with the rest of the device. Further, the fluid pathway concomitant must be equally small in diameter, so as to fittingly match the aperture in the needle. Such devices should ensure that alignment can be repeated every time the needle is retracted. There are problems here related to the tightness of the fluid communication between syringe body and the needle's aperture, and the resulting problems of hygiene and contamination, should fluid spill into the body of the device. There are also problems relating to the holding of a needle in a single position.

The attention of the reader is also drawn to prior art document U.S. Pat. No. 5,704,921A (CARILLI).

It is an aim of the invention to attempt to solve these and other problems.

SUMMARY OF THE INVENTION

In a first broad independent aspect, the invention provides an attachment for a parenteral device, the device comprising a body and an outlet for conveying fluid, the attachment comprising a housing adapted for engagement with said body, an elongate hollow needle, having an outer end and an inner end, with an aperture at both ends, a carrier for carrying said needle, said carrier being movable relative to said housing from a first position, at which said outer end is received within the housing, to a second position at which said outer end extends from the housing and said carrier being movable from said second position to said first position, and said housing having a flow path extending, when said carrier is in said second position, between said outlet and said carrier, wherein said needle is open at said inner end; whereby when said carrier is positioned in said second position said inner end is brought into communication with said flow path.

This represents a considerable advance over EP 0 613 382, wherein the needle utilised by the device must have a hole bored in the side. It should be considered inventive for a number of reasons.

Firstly, there is manifestly no need to go through the time and cost expenses of actually boring the hole into the needle.

Second, the invention at issue allows conventional needles to be used. This new design uses a conventional hollow needle with no side aperture formed in it. Instead the open inner end of the needle communicates directly with the attachment passageway which opens immediately above it. Thus there is no need to modify a conventional needle and nothing in patent specification EP 0 613 382 shows or suggests this construction.

In a subsidiary aspect, said carrier sealingly engages said housing in said second position.

This is advantageous in that the seal thus made allows for the constitution of a flow path free of leaks, with the result that a given parenteral fluid may be conveyed to its target without spillage, or contamination from external sources. It allows carrier itself to create a seal with said housing, there is therefore a reduction in the components necessary as compared to the prior art embodiment which requires multiple seals in addition to the needle's handle.

In a further subsidiary aspect, said carrier incorporates a cylindrical portion which holds said needle and which incorporates a side opening allowing said inner end of said needle to communicate with said flow path. This configuration allows the flow path to access the needle from the side of the needle without requiring the needle itself to incorporate a side opening. The side opening may be of a greater diameter than the diameter of the needle.

In a further subsidiary aspect, said housing incorporates a track in which said carrier is displaceable between said first position and said second position; and said carrier incorporates a jaw which releasably attaches to said housing at said first position and said second position. This configuration is particularly advantageous because it avoids having to rotate the needle and handle.

In a further subsidiary aspect, said housing incorporates an outlet which is in communication with said flow path when said carrier is in said first position.

A parenteral device so arranged as to keep the flow path open in the first position and seal the flow path in the second position is advantageous in that it allows for the inside of the housing to be optionally cleaned.

It also makes it easier to drain a given device quickly, because in the retracted position, a larger flow channel may be provided than in the extended position than would be the case if the flow path had to pass through the needle. With the needle retracted, the fluid may simply pass down the flow path and out of the device.

In a further subsidiary aspect, the attachment further comprises a collar which is secured in a recess of said housing; said collar incorporating an aperture which is sized and shaped to correspond to the nozzle of a parenteral device for frictionally gripping said nozzle.

A frictional gripping portion allows for attachment and device to be joined together quickly and easily.

In a further subsidiary aspect, said recess incorporates an outer rim and said recess incorporates a reduction in diameter within said opening; whereby when said collar is pushed into said recess the grip of said collar tightens.

In a further subsidiary aspect, said attachment further comprises releasable attachment means which secure said collar in a pushed in position in order for the collar to maintain its grip on the nozzle.

This feature is particularly advantageous because it may allow for the attachment and the device to be locked together, thus avoiding detachment through a light knock or suchlike.

The provision of a retainer is advantageous in that the needle held by the carrier will be held steadily, allowing for the precise use of the device. This is of particular benefit where the device is a syringe or catheter and the correct placement of the device is essential in order to minimise the discomfort caused to the subject by said placement.

It will be possible to lock the needle in the retracted position. This is particularly advantageous if it is desirable for the needle to be used once and then retracted, as when the user is dealing, for example, with infectious matter.

This is also advantageous in that it will allow for the disposal of the attachment without having to provide a separate "sharps" bin.

In a further subsidiary aspect, at least a portion of said housing is substantially transparent.

In a further subsidiary aspect, at least a part of the portion of the housing housing the needle is substantially transparent. This is particularly useful for the user who wishes to get a quick indication of the condition of the needle at any time.

In a further subsidiary aspect, said housing incorporates a resting surface located at an upper portion of said housing against which said body rests, when secured to said attachment, abutting the circumference of the body of the device without providing axial restraint.

This is advantageous in that the housing and the device may lend support to each other's position, giving stability and solidity to the device. In one configuration, it is envisaged that at the upper portion there is no attachment between the device and the housing whilst overall stability is achieved by the attachment at the nozzle of the device coupled with the body resting on the housing. It is further advantageous over the provision of a clip or lock in that mere resting contact does not hinder the quick removal or attachment of the attachment from the parenteral device.

BRIEF DESCRIPTION OF THE DRAWINGS

The invention will be more fully understood in the light of the following description of several specific embodiments. The description is made with reference to the accompanying drawings of which.

DETAILED DESCRIPTION OF THE FIGURES

Figure 2:
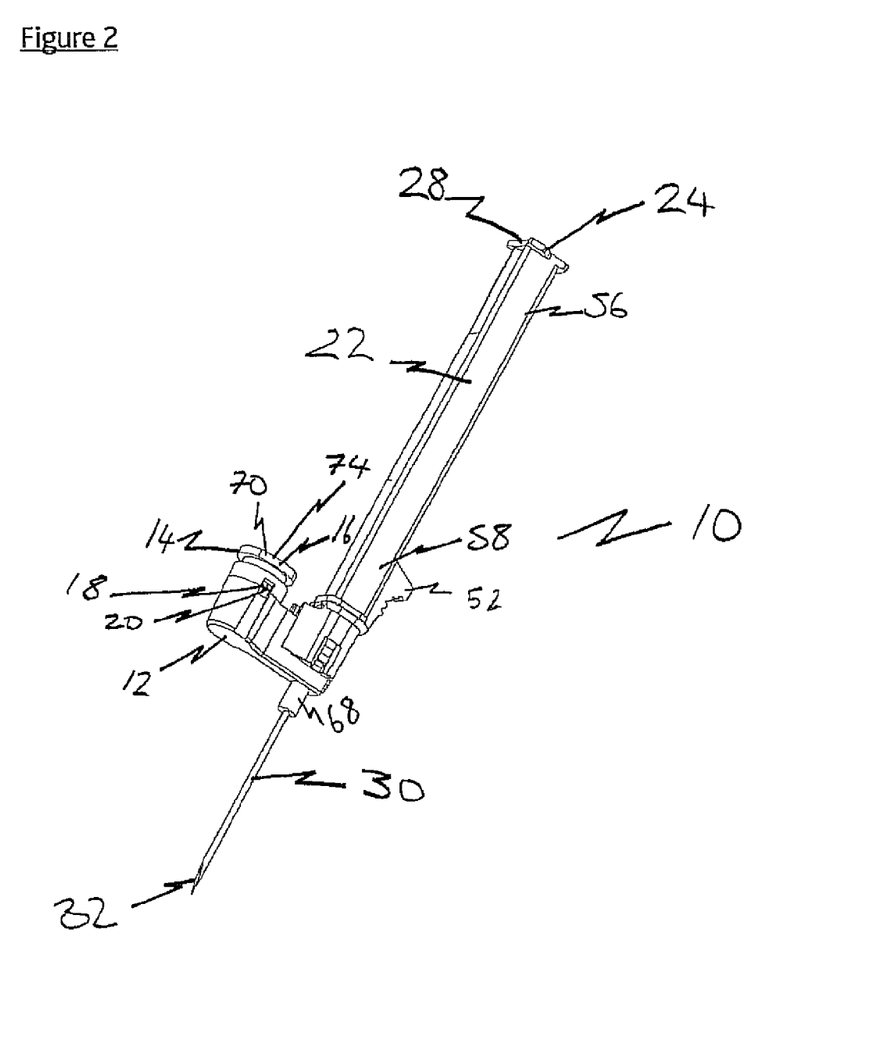
FIG. 2 is a perspective view of an attachment with the needle in its external position.
Figure 5:
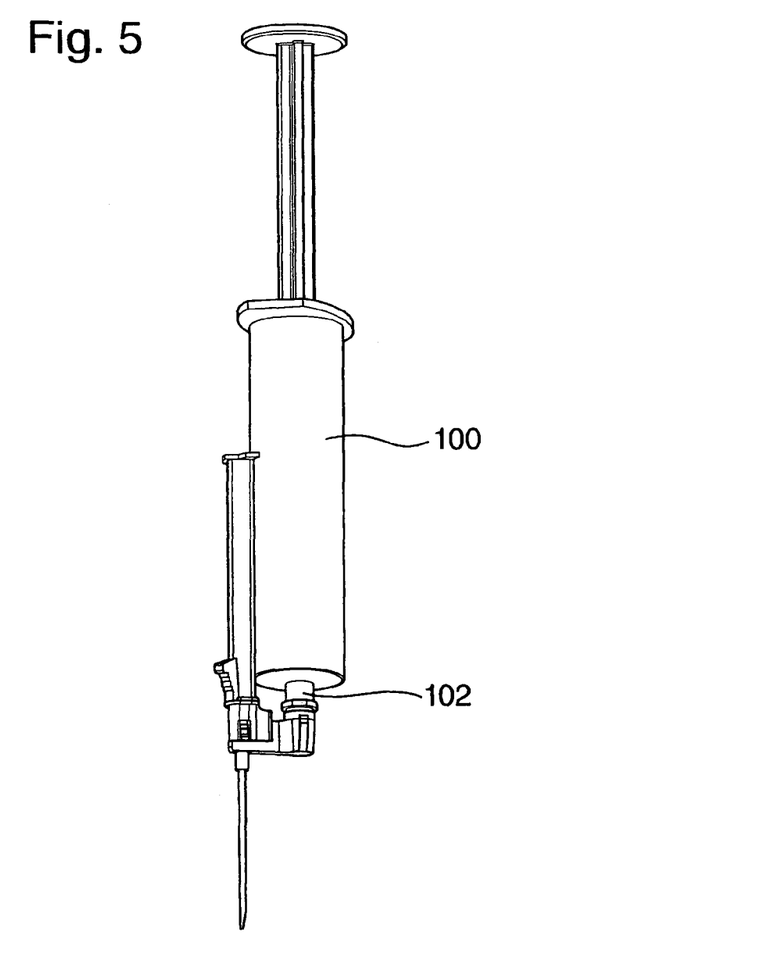
FIG. 5 is a perspective view of an embodiment of the invention with a syringe engaged to its housing.

FIG. 2 shows an embodiment of the invention generally indicated at 10. The invention is an attachment for a parenteral device. The parenteral device itself (which may be viewed at FIG. 5) comprises a body 100 and has egress means or an outlet or passageway 102 for conveying fluid. By parenteral device, it is meant any device which can be used for the conveyance of fluids which are to be introduced into or drawn from the body and/or object and shall include a syringe, a cannula, a hypodermic needle, an intravenous infusion line and like devices. This attachment 10 is adapted to fit with a conventional syringe body incorporating a nozzle.

The attachment 10 comprises a housing 12 adapted to be engageable with said body. The engagement takes place at only two sites. The first site 14 comprises a Luer connection with a collar 70 (FIG. 3 particularly) which is secured to the housing 12 in an opening 71 which reduces in diameter from its upper rim 72 to its base portion 73 so that when the collar is pushed into the opening the collar's diameter is reduced. When the nozzle of a parenteral device is placed into the collar and the collar is pushed into the opening the collar grips in effect the nozzle. The collar incorporates a lip 16 with a flat portion 74 allowing an operator to readily grab the collar and rotate it so that tabs 18 engage apertures 20 to secure the collar in position relative to the housing. When one of said tabs 18 comes into contact with the said tab-receiving aperture 20 it will form a releasable lock fit, locking the body to the attachment 10.

The connection between the body and the housing 12 need not be rigid. Indeed, it may be advantageous if said connection is flexible, particularly in embodiments where the body of the parenteral device is not directly connected to the housing 12 but instead is joined to housing 12 by a tube, for example in a situation where the attachment 10 has to be sited remotely from the parenteral device as when the fluid contained in the parenteral device is, for example, temperature sensitive and needs to be kept in a remote refrigerator. The second point of contact between the housing 12 and the body (not shown) is by means of the slider 22. The top 24 of the slider 22 features a groove or rest surface 28 so sized as to enable said slider 22 to rest on the body of a parenteral device attached to the attachment. The resting surface 28 abuts the circumference of the body 100 of the device without providing axial restraint. The resting surface has a curved syringe body contacting face which, in use, provides for greater support than a flat rest. It some embodiments, the resting surface 28 will have a surface made of a non slip material, or be otherwise roughened in order to maximise the gripping qualities of said material. The slider 22 is substantially transparent. Other embodiments of the attachment 10 are envisaged where only a portion of the slider 22 is transparent or where the slider 22 is entirely opaque.

In this embodiment the Luer device at the first site 14 is releasably lockable. Although this embodiment features a Luer device other releasable locking means may be envisaged. Indeed, a non-locking frictional fit may be advantageous.

Figure 3:
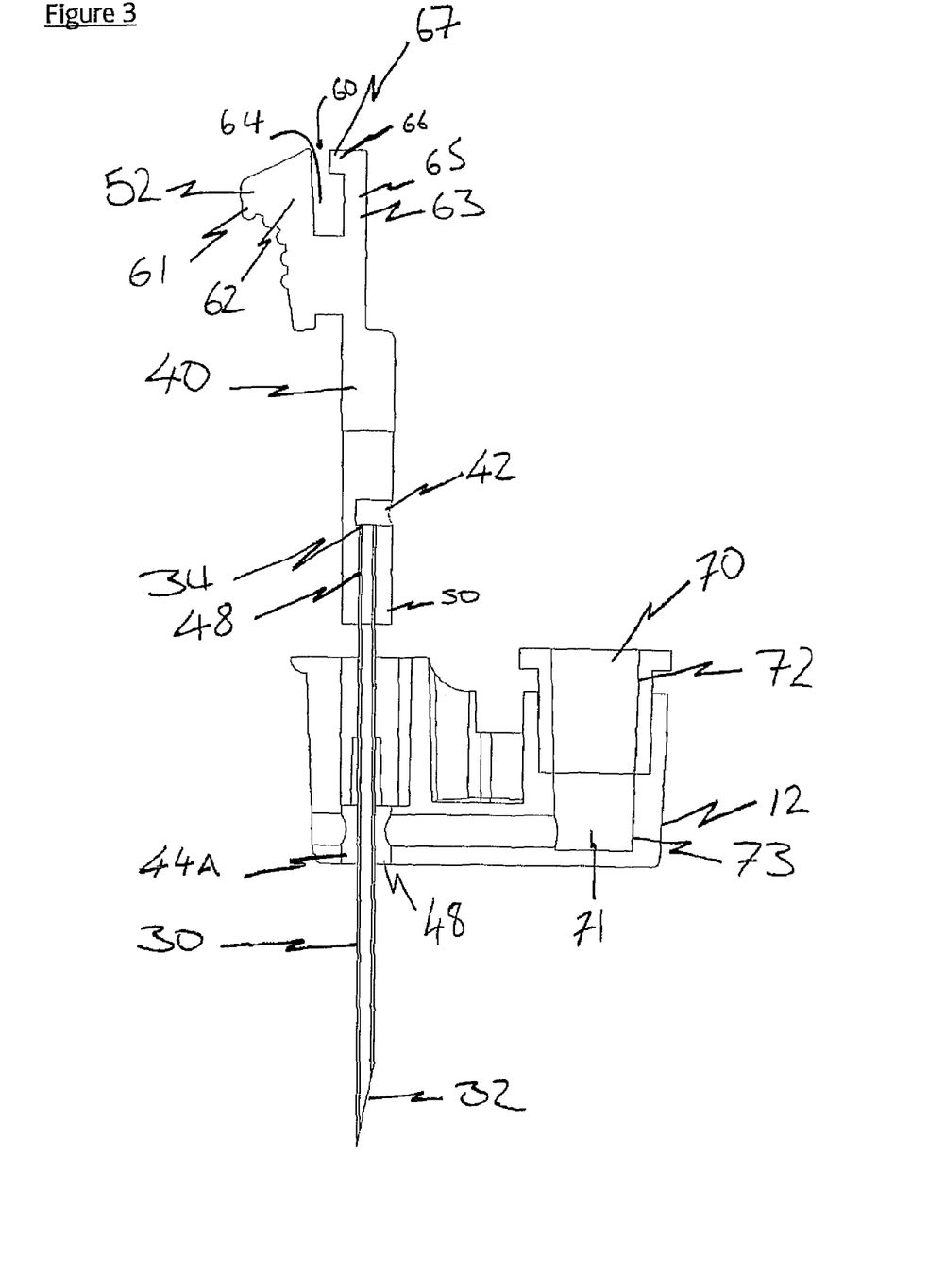
FIG. 3 is a cross-sectional side view of an embodiment of the invention with a part of the housing removed with the needle and carrier between their inward most retracted position and their outward most projecting position.
Figure 4:
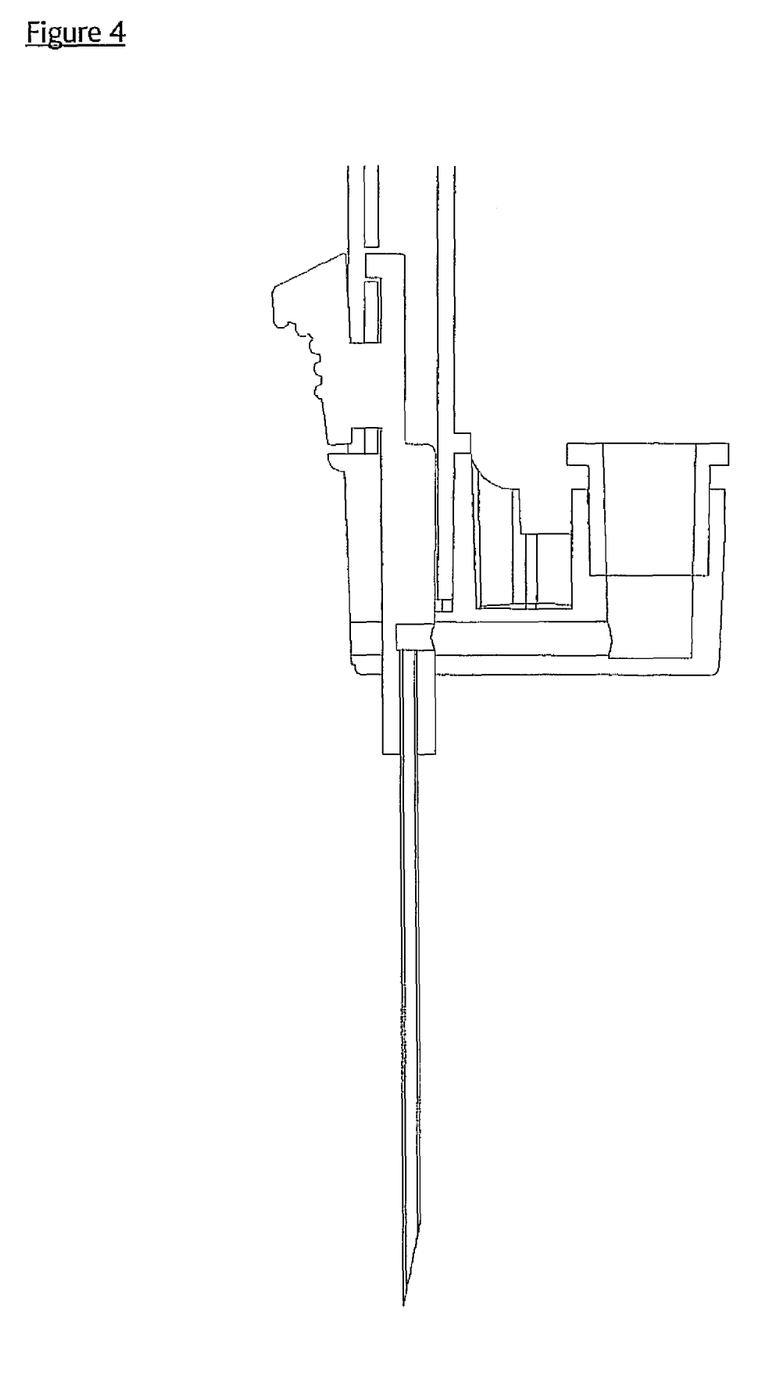
FIG. 4 is a cross-sectional side view of part of an embodiment of the invention with part of the needle and carrier assembly in communication with the flow path (in their outward most projecting position).

Device 10 further features an elongate hollow needle 30 with a first end 32 which is sufficiently sharp for insertion into a body and/or object and a second end 34 which is relatively blunt, which can be seen on FIG. 3. Each of the two ends 32 and 34 has a single aperture 36, 38. It is, however, envisaged that either or both the ends could feature more than one aperture.

An attachment according to any of the previous claims, wherein said housing incorporates a resting surface located at an upper portion of said housing against which said body rests, when secured to said attachment, abutting the circumference of the body of the device without providing axial restraint.

At FIG. 3 is shown the carrier 40. The carrier 40 is adapted to receive the second end 34 of the needle 30, having a passageway so sized and constructed out of appropriate materials to define a passageway 48 which forms a frictional fit around the diameter of a needle 30. The carrier 40 is made substantially of a plastics material, The carrier 40 is moveable from a first position, where the first end is received within the housing 12 and a second position, in which the first end extends from the housing 12. Movement from the second position to the first position is also possible. The needle receiving portion 50 of the carrier 40 is so sized as to form a seal when engaging passage way 44A. Both are of similar shape such as circular to create a tight fit between the cylindrical needle receiving portion 50 and the passage way 44A. Due to the tight fit there is no need for additional seals such as O-rings as would be necessary in the prior art between the housing and the needle.

The sealing engagement thus achieved allows the flow of fluid into flow path 42 of the carrier 40. The passageway 44A is left open at one end 46 when the needle is moved into the first position meaning that the egress means which here is a passageway 44A is open and fluid travelling down the egress means from the aperture defined by the lip 16 will flow out of the aperture 48.

Figure 6:
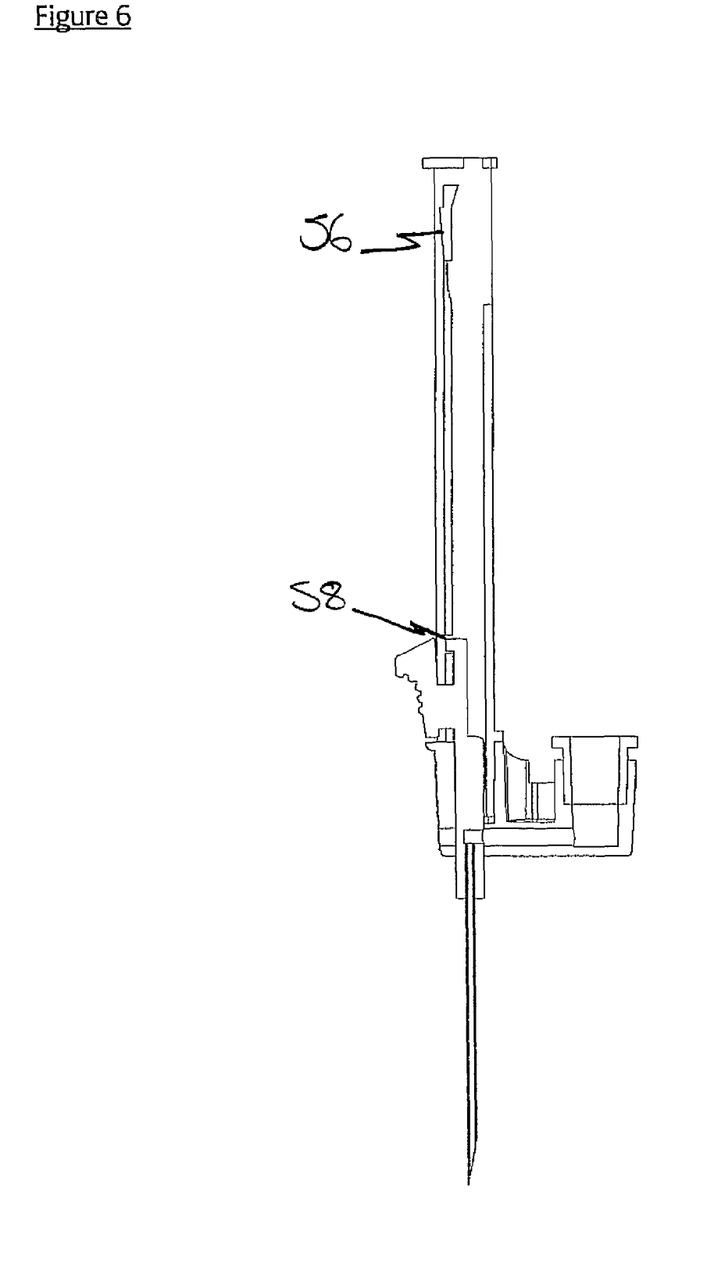
FIG. 6 is a cross-sectional side view of an embodiment of the invention with part of the needle and carrier assembly in communication with the flow path (in their outward most projecting position).
Figure 7:
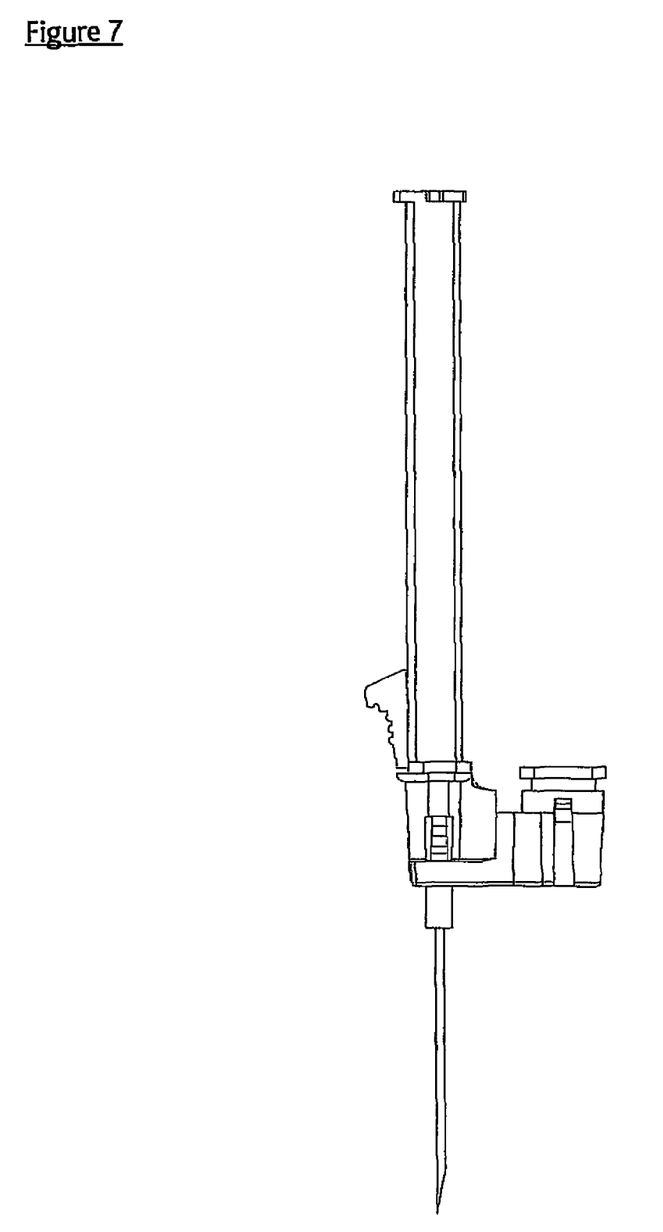
FIG. 7 is a side view of an embodiment of the invention with part of the needle and carrier assembly in communication with the flow path (in their outward most projecting position).
Figure 8:
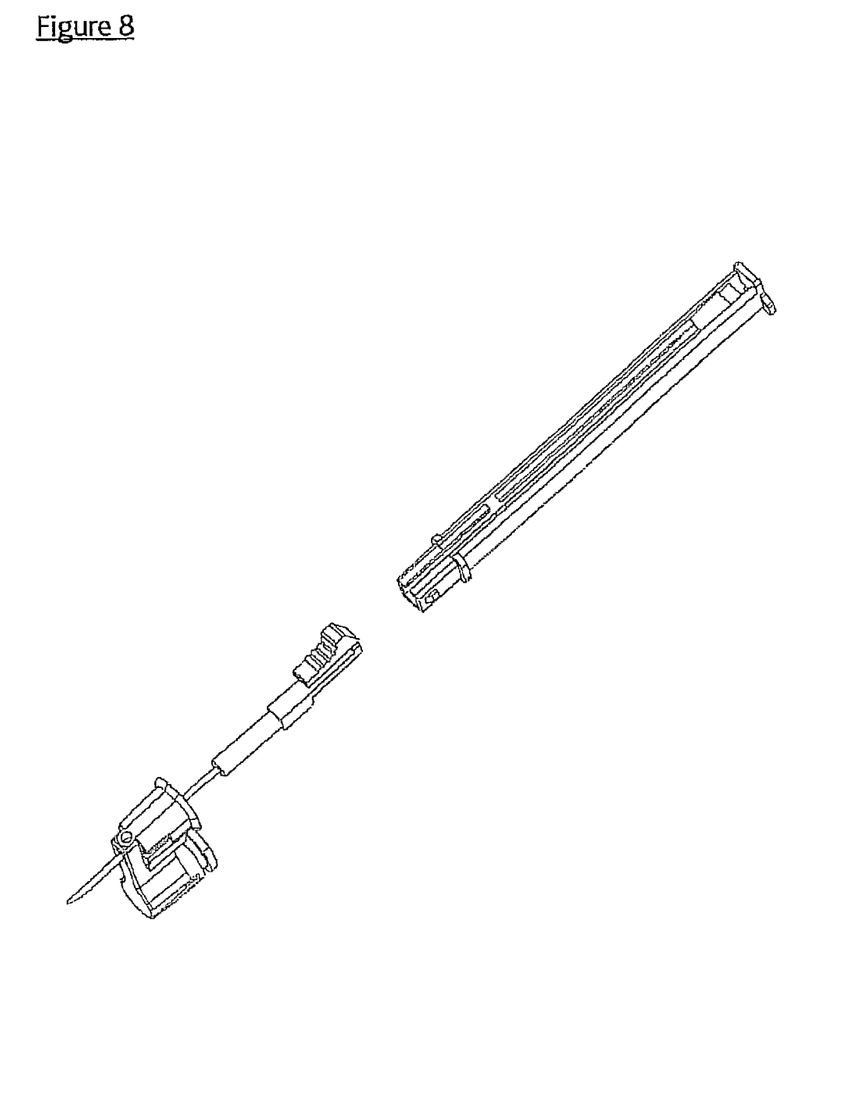
FIG. 8 is an exploded perspective view of an embodiment of the invention with a part of the housing removed with the needle and carrier between their inward most retracted position and their outward most projecting position.
Figure 9:
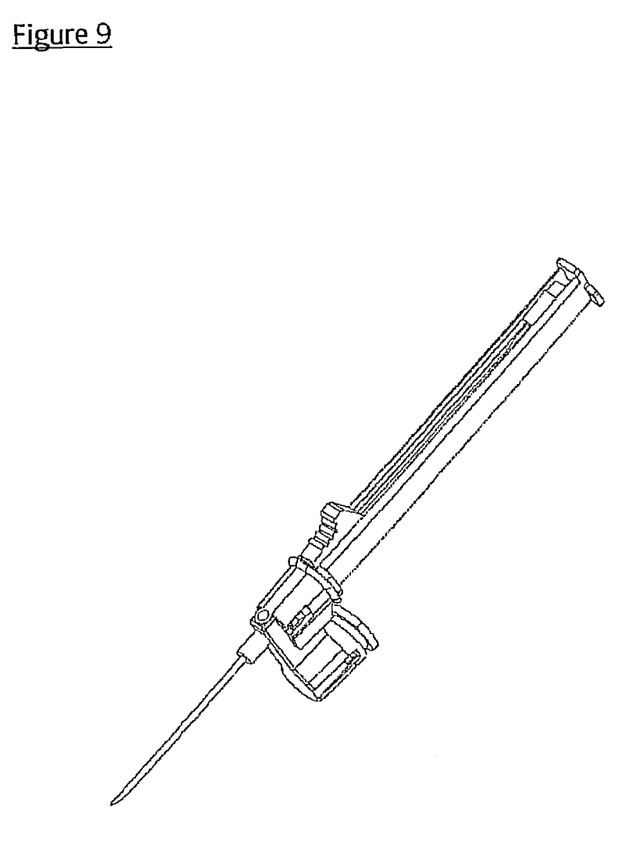
FIG. 9 is a perspective view of the invention with part of the needle and carrier assembly in communication with the flow path (in their outward most projecting position).
Figure 10:
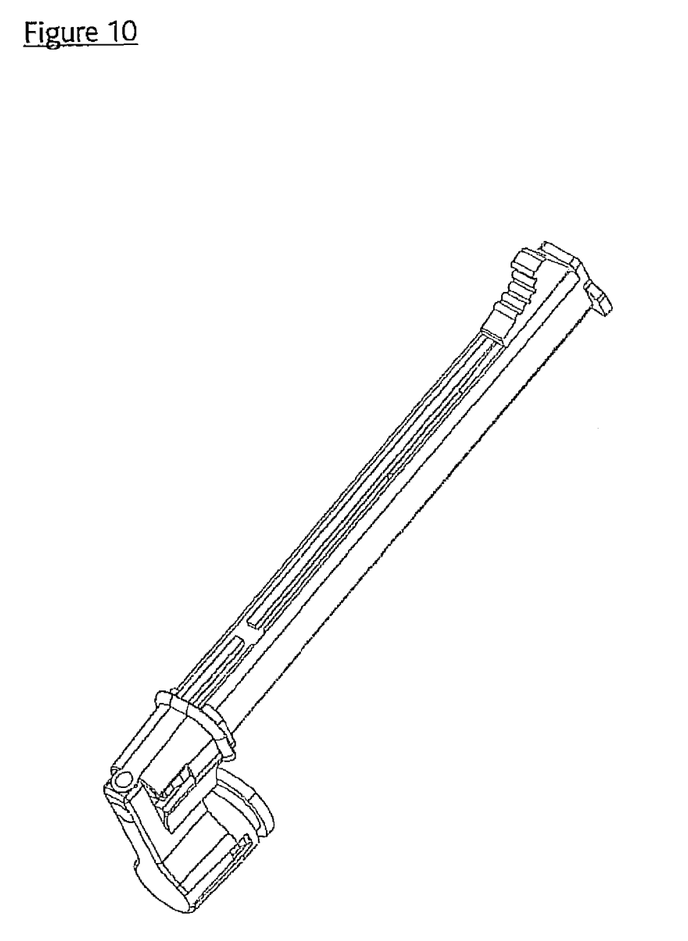
FIG. 10 is a perspective view of the invention with the need and carrier fully retracted into the body.

The carrier 40 (FIG. 2 or FIG. 3) further comprises a button 52 incorporating a jaw 60 for releasably immobilising the carrier 40 in a given position relative to the housing. Jaw 60 (FIG. 3) incorporates an outwardly projecting portion 61 with a serrated or knurled outer edge which is ergonomically bowed and which increases in lateral extension from bottom to top in order to facilitate the retraction of the needle by the operator. Jaw 60 incorporates a first half 62 which incorporates the projecting portion and a second half 63 which are separated by a gap 64. The second half 63 incorporates a beam 65 which is free at extremity 66 and which incorporates an inward projection 67 which acts as a stop when located in abutment into an appropriately sized receiving portion. The housing comprises two receiving portions 56 58 (best viewed at FIG. 6); one receiving portion 56 corresponding to the first position when the first end 32 is receiving the housing 12 and the other receiver 58 corresponding to the second position at which the first end 32 extends from the housing 12. In FIG. 2, the button 52 is inter-engaged with the second receiver 58 and the needle 30 is therefore in the second position. In order to remove the button from the second receiver 58, the operator applies pressure onto the button in order to deflect it inwards. Projection 67 is then free from receiving portion 58 to allow the retraction of the carrier and needle towards receiving portion 56.

In alternative embodiments it may be possible to permanently lock the carrier 40 in a given position. In such embodiments it is envisaged that one or more of the receiving portions 56, 58 will further comprise permanent locking means. This will be of advantage for one shot syringe attachments whereby it is desired to permanently enclose the needle 30 after a single use.

The needle 30 may be detached from the carrier 40 thereby allowing for easy replacement. The needle 30 may alternatively be permanently fixed.

In the position where the needle 30 and carrier 40 are extended, both a portion of the needle 30 and a portion 68 of the carrier extend beyond the housing.

In alternative embodiments passageway 44A is provided with a cap, which may be separate or hinged or otherwise connected to the housing 12. This cap will be so sized as to sealingly engage with passageway 44A, and may be freely engaged and disengaged with the passageway 44A by the user, as long as neither needle 30, nor carrier 40 are blocking the seal.

For the avoidance of doubt, the use of the term "conventional syringe body" in the claims encompasses conventional bodies of parenteral devices of all sorts.

The invention claimed is:

1. An attachment for a parenteral device, adapted to fit with a conventional syringe body the device comprising a body and an outlet for conveying fluid, the attachment comprising:
   a housing adapted for engagement with said body;
   an elongate hollow needle, having an outer end and an inner end, with an aperture at the extremity of each end and incorporating an opening located above said extremity;
   a carrier for carrying said needle, said housing having a flow path extending, when said carrier is in a position in which it extends from said housing, between said outlet and said carrier;
   wherein said needle is open at said inner end; whereby when said carrier is in said position in which it extends from said housing, said carrier's opening and thus said inner end is brought into communication with said flow path; and wherein said carrier is movable, by an operator, relative to said housing from a first position, at which said outer end is received within the housing, into and out of said position- a second position - at which said outer end of said needle extends from the housing.

2. An attachment according to claim 1, wherein said carrier sealingly engages said housing in said second position.

3. An attachment according to claim 1, wherein said carrier incorporates a cylindrical portion which holds said needle and which incorporates a side opening allowing said inner end of said needle to communicate with said flow path.

4. An attachment according to claim 1, wherein said housing incorporates an outlet which is in communication with said flow path when said carrier is in said first position.

5. An attachment according to claim 1, wherein said housing incorporates a track in which said carrier is displaceable between said first position and said second position; and said carrier incorporates a jaw which releasably attaches to said housing at said first position and said second position.

6. An attachment according to claim 5, wherein the jaw incorporates an outwardly projecting portion in order to facilitate the retraction of the needle by the operator.

7. An attachment according to claim 1, wherein at least a portion of said housing is substantially transparent.

8. An attachment according to claim 1, wherein said housing incorporates a resting surface located at an upper portion of said housing against which said body rests, when secured to said attachment, abutting the circumference of the body of the device without providing axial restraint.

9. An attachment according to claim 1, further comprising a collar which is secured in a recess of said housing; said collar incorporating an opening which is sized and shaped to correspond to the nozzle of a parenteral device for frictionally gripping said nozzle.

10. An attachment according to claim 9, wherein said recess incorporates an outer rim and said recess incorporates a reduction in diameter within said opening; whereby when said collar is pushed into said recess the grip of said collar tightens.

11. An attachment according to claim 10, further comprising releasable attachment means which secure said collar in a pushed in position in order for the collar to maintain its grip on the nozzle.

12. An attachment according to claim 1, wherein there is an aperture at the extremity of each end only.

13. An attachment according to claim 1, wherein the needle further comprises a continuous side wall with no side aperture formed in it.

* * * * *